Oct. 1, 1968 W. E. LAMMERTS Plant Pat. 2,838
ROSE PLANT
Filed May 29, 1967
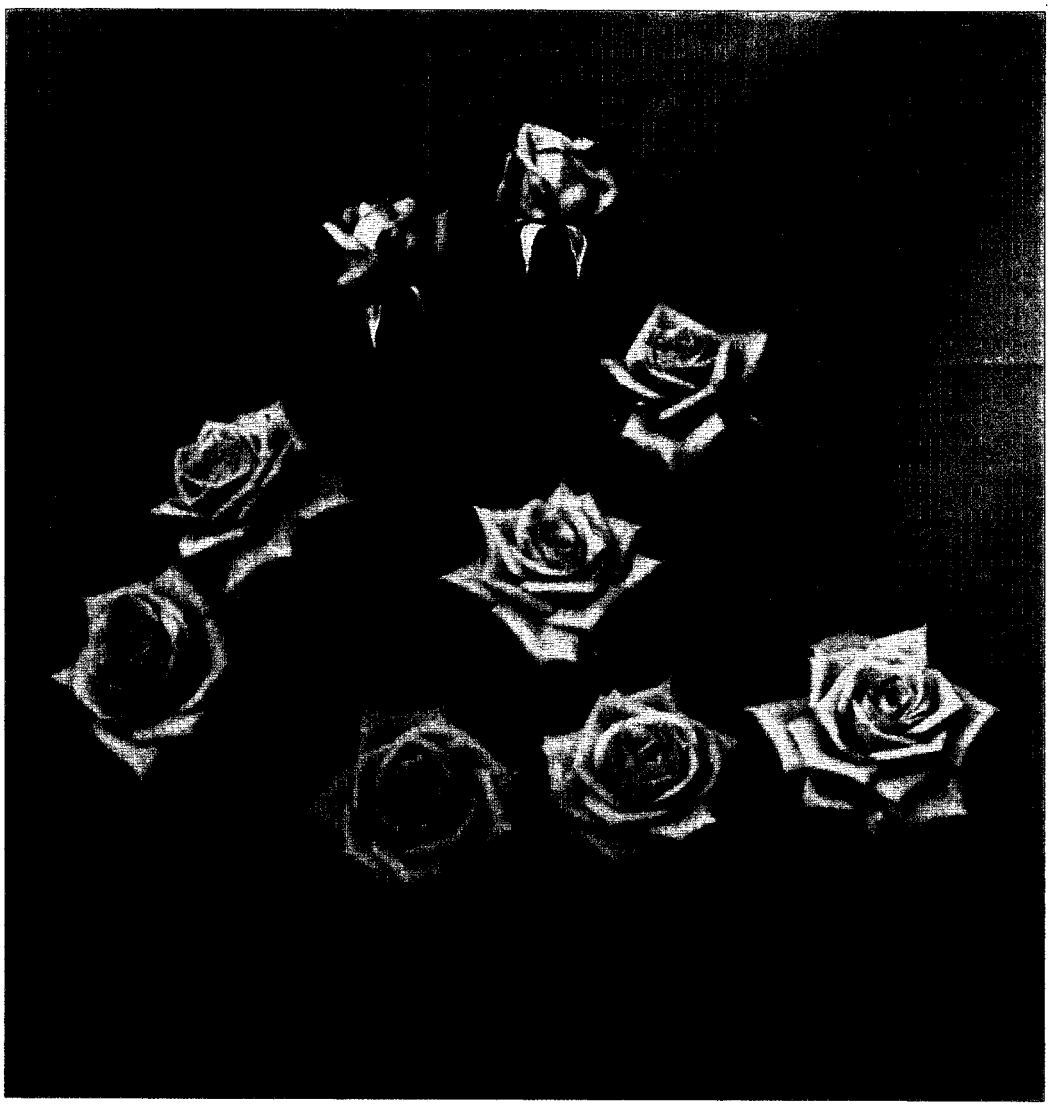
INVENTOR
WALTER E. LAMMERTS
BY Rummler & Snow
Attys

United States Patent Office

Plant Pat. 2,838
Patented Oct. 1, 1968

2,838
ROSE PLANT

Walter E. Lammerts, Freedom, Calif., assignor to Amling-DeVor Nurseries, Inc., Livermore, Calif., a corporation of California Filed May 29, 1967, Ser. No. 642,248
1 Claim. (Cl. Plt.—29)

ABSTRACT OF THE DISCLOSURE

A new variety of rose plant bearing velvety rich red, non-blueing, slow opening flowers of great substance borne individually on long well proportioned stems; this new variety being a large flowered floribunda with high winter production and rapid cycling of bloom periods.

*Background of the invention.*—This new variety of rose plant originated as a seedling of the variety Christian Dior (Plant Patent 1943), the pollen parent being Rumba (Plant Patent 1919), and was developed by me in 1963 during the course of a breeding program carried on by me at Livermore, Calif. since 1955 with the object of producing an improved long stemmed red rose suitable for greenhouse culture for commercial cut flower production. The new plant was observed to possess unusual and valuable characteristics in that it produced profusely very attractive, high centered blooms having extra-long-lasting quality, both on the plant and as a cut flower. The new plant was found to flower continuously, during all seasons, and to be little affected by wet or hot weather. Also the plant was found to have a free branching and vigorous growth habit, producing long straight stems and abundant foliage, and being of upright compact form averaging 30 to 36 inches in height.

This new variety of red rose plant has been asexually reproduced by me and under my direction at Livermore, Calif. and successive generations produced by budding have demonstrated that the novel and advantageous characteristics of the new variety are fixed and hold true in all respects from generation to generation. Propagation and field testing has also been done at Hamilton City, Calif. and Phoenix, Ariz., and commercial scale propagation is now being done at these places as well as at Livermore, Calif.

*Description of the drawing.*—My new variety of rose plant is illustrated in the accompanying full color drawing which shows typical specimens of partially opened and fully opened flowers together with some of the foliage of the new plant.

*Description of the new plant variety.*—The following is a detailed description of my new variety of rose plant with color designation according to the Horticultural Colour Chart for the British Colour Council.

*The plant*

Origin: Seedling.
Parentage:
*Seed parent.*—Christian Dior (Plant Patent 1,943).
*Pollen parent.*—Rumba (Plant Patent 1,919).
Classification:
*Botanic.*—*Rosa odorata* hybrid.
*Commercial.*—Floribunda.
Form: Bush, upright and compact.
Height: 30 to 36 inches in garden.
Growth: Vigorously active.
Branching: Free.
Strength: Very strong slender upright canes.
Foliage:
*Quantity.*—Abundant, 7 to 10 leaves below the flower.

*Size of leaf.*—4 to 6 inches long.
*Shape.*—Pinnate.
*Leaflets.*—Ovate-accuminate, 1"–2½" long by ½"–1½" wide; 3 to 7 in number, averaging 5.
*Texture.*—Moderately leathery, smooth and finely serrated.
*Color.*—Mature leaf: upper side—Spinach Green 0960, often overlain Garnet Lake 828/2; underside—Lavender Green 000761, often overlain Garnet Lake 828/2.
*Ribs and veins.*—Conspicuous, often reddish.
*Petrioles.*—½" to 1½" long.
*Rachis.*—Slender, 2¼" to 3½" long.
*Thorns.*—Descending, but not hooked. Color—Rhodonit Red 0022/3, when thorns are young, tan when old. Size—slender, ¼" to 5/16" long.

*Bud*

Form: Classical hybrid tea—urn-shaped, long and pointed.
Size: Small, ¾"–13/16" in diameter, ¾"–13/16" deep.
Opens slowly.
Color: Very dark Cardinal Red 822 with dark Dahlia Purple reflexes 931 when sepals first divide. Dark Cardinal Red 822 with Dahlia Purple markings on guard petals when sepals begin to unfurl.
Sepals: Narrowly Lanceolate shaped, 3/16"–¼" by ⅝"–1" in size. Margins and tips often ornate-fimbriate. Sepals curl back.
Color: inside—Spinach Green 0960/5; outside—Lettuce Green 861/1.
Calyx:
*Shape.*—Goblet.
*Size.*—Small, 9/32"–11/32" broad by 11/32" long.
*Aspect.*—Smooth. Does not split.
Peduncle: Length—3¼"–4¾". Slender, erect, strong and wiry, with sparse prickles. Color—Lettuce Green 861.

*The flower*

Blooming habit: Continuous, blooming profusely during all seasons.
Size: Small, ¾"–13/16" in diameter, ¾"–13/16" deep.
Borne: Singly and in clusters of 3 to 5 blooms.
Shape: High center when bloom first opens, later the petals reflex and quill.
Petalage: 30 to 40, in whorled-imbricate arrangement.
*Form.*—Broadly round and accuminate.
*Color.*—Outer and inside petals—Cardinal Red 822, underlain Buttercup Yellow 5/2, Buttercup Yellow 5/2 at base. Reverse side—Cardinal Red 822/1.
Petaloids: 4 to 6 in number, ⅜"–½" by ¼"–⅝" in size. Color—same as petals, but with white midrib.
Texture: Moderate leathery. Appearance—velvety.
Discoloration: Becomes darker after full bloom.
Fragrance: Moderate—apple and cedar.
Lasting quality: On plant—very long, 10–12 days. As a cut flower—very long, 5–8 days.
Peduncle: 3¼"–4¾" long; sturdy and strong, upright and stiff. Color—Dark Lettuce Green 861.
Disease resistance: Moderately resistant to mildew, rust and black spot as observed in growing fields at Livermore and Hamilton City, Calif. and Phoenix, Ariz.

*Genital organs*

Stamens:
*Anthers.*—About 65 to 75 in number, 3/32" long, and in whorled arrangement.
*Filaments.*—⅛" to ¼" long and red in color.
Pollen: Yellow in color.
Pistils: About 40 in number, 3/32"–¼" long.
Stigmas: White in color.
Ovaries: Ordinary in character.

*Fruit*

The fruit is fertile, ovoid in shape and is of an Orient Red Color 819 at maturity.

My new red rose plant variety most nearly resembles Garnette Supreme (Plant Patent 1,318). Differences from Garnette Supreme, however, are found in that the new variety has stems that are straighter and from 30 to 40% longer; has 30 to 40% greater peduncle length; a longer and more slender bud, with no flats; a larger open flower of brighter color, free from magenta and with velvety petal texture; and has much less tendency to throw clusters.

The new variety also resembles Tommy Bright (Plant Patent 2,129) in general appearance but differs from Tommy Bright by producing blooms of brighter color, with less magenta, and with better proportioned stems and foliage growth. Also, my new variety has bright, pointed buds as compared with the dark, flat buds of Tommy Bright, has better keeping quality for its blooms and is faster cycling in its blooming habit.

I claim:

1. A new and distinct variety of rose plant substantially as herein shown and described, characterized by its velvety rich red, non-blueing, slow opening flowers mostly borne individually on long stems and possessing exceptionally long vase-life; and by the rapid cycling of its bloom period and its high winter production.

No references cited.

ROBERT E. BAGWILL, *Primary Examiner.*